US 6,554,649 B2

(12) United States Patent
Pade

(10) Patent No.: US 6,554,649 B2
(45) Date of Patent: Apr. 29, 2003

(54) COMPACT COUPLER PLUG, IN PARTICULAR FOR A PLANAR BROADBAND LAMBDA SENSOR

(75) Inventor: Wolfgang Pade, Illingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/004,943

(22) Filed: Dec. 3, 2001

(65) Prior Publication Data
US 2002/0111071 A1 Aug. 15, 2002

(30) Foreign Application Priority Data
Dec. 1, 2000 (DE) .......................... 200 20 379

(51) Int. Cl.[7] .............................................. H01R 13/66
(52) U.S. Cl. ...................................... 439/620; 439/913
(58) Field of Search ........................ 439/79, 492, 637, 439/620, 59, 494, 652, 651, 76.2; 174/52.1, 913

(56) References Cited

U.S. PATENT DOCUMENTS

| 3,611,247 A | * | 10/1971 | Adams et al. ............. 439/106 |
| 5,108,315 A | * | 4/1992 | Vogl et al. ................ 439/639 |
| 5,435,735 A | * | 7/1995 | Wittig et al. ............. 439/637 |
| 5,703,754 A | * | 12/1997 | Hinze ....................... 174/52.1 |
| 6,132,256 A | * | 10/2000 | Morsdorf et al. .......... 439/620 |

* cited by examiner

Primary Examiner—Lynn D. Feild
Assistant Examiner—Phuong Dinh
(74) Attorney, Agent, or Firm—Kenyon & Kenyon

(57) ABSTRACT

In order to create a very small and compact embodiment of a coupler plug, in particular for a planar broadband Lambda sensor, a coupler plug is created for connecting a cable harness to a Lambda sensor. The coupler plug includes a housing, namely a basic element and a cover element. The coupler plug also includes electrical components that can be inserted into the housing and can be fixed in position. Additionally, the coupler plug includes an adjustment element for a sensor, in particular a planar broadband Lambda sensor, which can be arranged in the coupler plug or can be provided outside the coupler plug via a further contact element. Part of the coupler plug is designed as a contact carrier. Electrical contacts of the coupler plug and the adjustment element are pre-mounted on the contact carrier. It is possible to separate the contact carrier, along with the electrical contacts and the adjustment element, from the rest of the coupler plug.

21 Claims, 3 Drawing Sheets

COMPACT COUPLER PLUG, IN PARTICULAR FOR A PLANAR BROADBAND LAMBDA SENSOR

FIELD OF THE INVENTION

The present invention relates to a coupler plug that includes a housing, namely a basic body and a cover element, a sensor unit having electrical contact elements, in particular for a planar broadband Lambda sensor, and an adjustment element that is connected to the sensor unit.

BACKGROUND INFORMATION

Generally, coupler plugs of the aforementioned type are designed as Lambda sensors, the connectors that are provided in the coupler plug being provided for adjustment, signals, and heating the sensor. Conventionally, the Lambda sensor and the Lambda regulator, in conjunction with a three-way catalytic converter, constitute an effective method for cleaning exhaust gas. The Lambda sensor, which is for example screwed into an exhaust gas system, includes a measuring sensor for determining the oxygen content in the exhaust gas. The residual oxygen content is very suitable for use as a measured quantity and regulates the air-fuel ratio, as it indicates precisely whether the air-fuel mixture is combusting completely.

Herein, the Lambda sensor sends a voltage signal, which represents the current value for the composition of the mixture and tracks changes in the mixture. The fuel supplied to the engine is regulated by a mixture preparation system as a function of the Lambda sensor signal, so that a stoichiometric air-fuel ratio of $\lambda=1$ is achieved. Depending on the design of the exhaust gas system and the application, heated or non-heated sensors are used. Lambda sensors can also be used in applications other than fuel-powered vehicles, e.g., in order to regulate gas-powered engines or oil/gas burners.

Broadband Lambda sensors are modular in design, and in conjunction with planar technology allow a plurality of functions to be integrated. As a rule, they have function layers that include a porous protective layer, an outer electrode, a sensor foil, an inner electrode, a reference air channel foil, an insulating layer, a heater, a heating foil, and connector contacts.

As the broadband Lambda sensor includes a combination of a Nernst concentration cell (=sensor cell) and a pump cell that transports oxygen ions, it can take very precise measurements, not only at the stoichiometric point where $\lambda=1$ but also in the lean and rich ranges.

Each sensor must be individually adjusted. To accomplish this, the sensor has an installed resistor (mini-hybrid). Adjustment, which is preferably carried out using a laser beam, is carried out by removing as necessary the resistor layer that is provided on a ceramic substrate, this resulting in a change in the resistance, adjustment thus being accomplished.

Until now, adjustment has been carried out by bringing the housing of the coupler plug in which the resistor is installed to the adjustment location without the cover element. The cover element is put on after adjustment, via laser processing, has been performed.

To keep moisture, dirt, or similar from penetrating the coupler plug, the cover element has additional seals.

One disadvantage of the conventional embodiment of the coupler plug described above is that additional operation steps and assembly steps are required to close off the coupler plug in the functionally correct manner following adjustment.

Furthermore, an additional cover element along with a seal has to be manufactured and made available in the area where adjustment is performed.

SUMMARY

One object of the present invention is to create a further refinement of an embodiment of the coupler plug that is suitable in particular for applications where a planar broadband Lambda sensor is used, so that the coupler plug can be manufactured very inexpensively and has very small dimensions.

This object is achieved by designing part of the coupler plug as a contact carrier, electrical contacts of the coupler plug and the adjustment element being pre-mounted on the contact carrier, and it being possible to separate the contact carrier, along with the electrical contacts and the adjustment element, from the rest of the coupler plug.

An advantage of the present invention is that the coupler plug can be manufactured very inexpensively due to the compactness of the parts to be produced. As a result, the entire coupler plug can be pushed into a grooved tube due to its small size and small outer dimensions.

Moreover, in an example embodiment of the present invention, the same components, in particular for the plurality of electrical contact elements that are to be provided in the housing of the coupler plug, are used. This simplifies the assembly process.

It is advantageous that part of the coupler plug may be designed as a contact carrier, electrical contacts of the coupler plug and the adjustment element being pre-mounted on the contact carrier, and it being possible to separate the contact carrier, along with the electrical contacts and the adjustment element, from the rest of the coupler plug. Alternatively, the electrical contacts only are already arranged in the contact carrier. This can be accomplished, for example, by mounting them by pressing them in or by injecting plastic around them.

For assembly, it may be advantageous that the contact carrier, as a pre-assembled component, can be joined to the rest of the coupler plug without additional tools. Guide elements may be provided to ensure the contact carrier is positioned correctly, and stop-lock means are provided to fix it in place.

A further component, e.g., a secondary interlock element, may be arranged between the contact carrier and the rest of the coupler plug. This constitutes a connecting element between the contact carrier and the rest of the coupler plug, and also ensures that the electrical contacts are positioned correctly in terms of their position and function.

As the basic carrier is completely surrounded by the cover element, the interior of the sensor unit can be sealed off via an arrangement of sealing lips inside the cover element or an arrangement of seals on the basic carrier, so that the interior is protected against sprayed water and/or dirt, for example.

In addition, this helps lock the basic body to the cover element. Initial locking and final locking, i.e., primary interlocking and secondary interlocking, may be provided. The secondary interlock element performs the function of secondary interlocking.

Primary interlocking is carried out in two stages. In a first stage, the cover element is locked so that it is held on the basic body. Then, when the cover element is subjected to further pressure in the direction of the basic body, the secondary interlock element, which has been inserted into the basic body, is fixed in position against the electrical contact element that is guided in the basic body, e.g., a flat female terminal, and is connected to the Lambda sensor. However, this fixing in position is carried out only so that the secondary interlock element is pressed against the contact element, so that a firm connection is created between the contact element and the secondary interlock element. The secondary interlock element is held in the basic body subject to a positive lock, i.e., when the contact element is in the fixed state, the secondary interlock element can only move in the axial direction of mounting of the cover. Support elements that point away from the secondary interlock element are also provided on the secondary interlock element, these extending in the direction of the cover element.

When the secondary interlock element is in the non-operated state, i.e., the contact element has not been fixed in position, the support elements extend well beyond the coupler plug's basic body, so that the cover element can only complete the first locking stage of primary interlocking. Thus, the cover element can only complete the second locking stage of primary interlocking if complete operation has been performed and the contact element has been correctly fixed in position. This has the advantage that a check can easily be performed as to whether a good contact has been created successfully and the electrical contact element is also reliably secured to the Lambda sensor, and whether the cover element has closed off the basic body with a tight seal.

It may be advantageous if the securing devices are provided at the edge of the cover element, thus allowing the coupler plug to be attached to a further component, e.g., via a groove-tongue connection; or alternatively securing devices are designed so that electrical lines can be attached to the coupler plug.

An arrangement for attaching spray water grommets can be provided as an optional feature.

Another advantage of the present invention is that the aforementioned seals can be injection-molded onto the cover element so that they cannot be lost.

To ensure the transition resistance between the sensor unit and the electrical contact elements remains constant, a soldered join may be provided.

In the example embodiment, it is advantageous that the cover element is made of PBT (polybutylene terephthalate) or equivalent materials.

DETAILED DESCRIPTION

Figure 1:
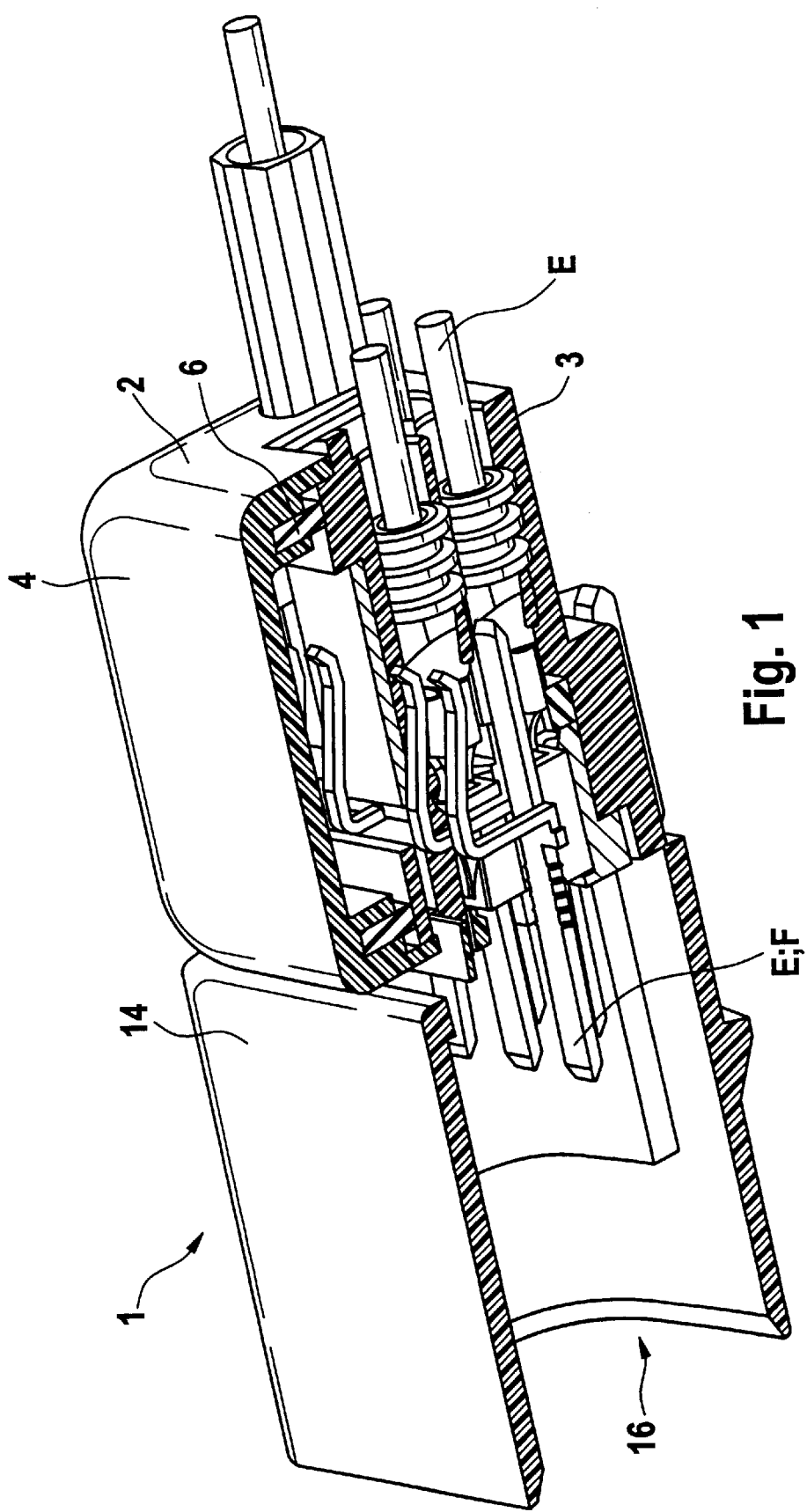
FIG. 1 shows a perspective view of an example cable harness plug according to the present invention having a closed cover element, the contact carrier having been inserted, in section view.
Figure 2:
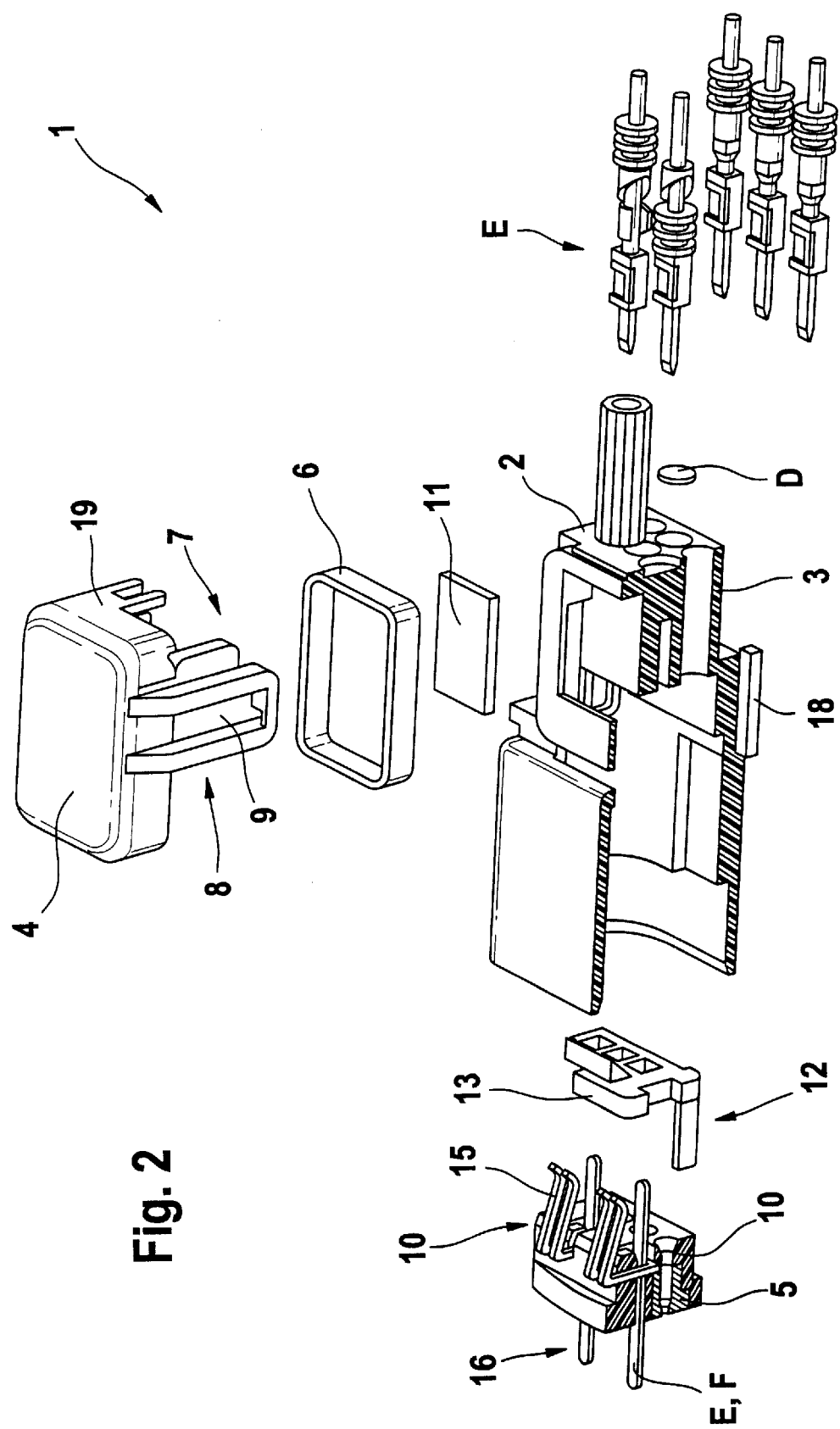
FIG. 2 shows a perspective view of the individual components of the coupler plug shown in FIG. 1.
Figure 3:
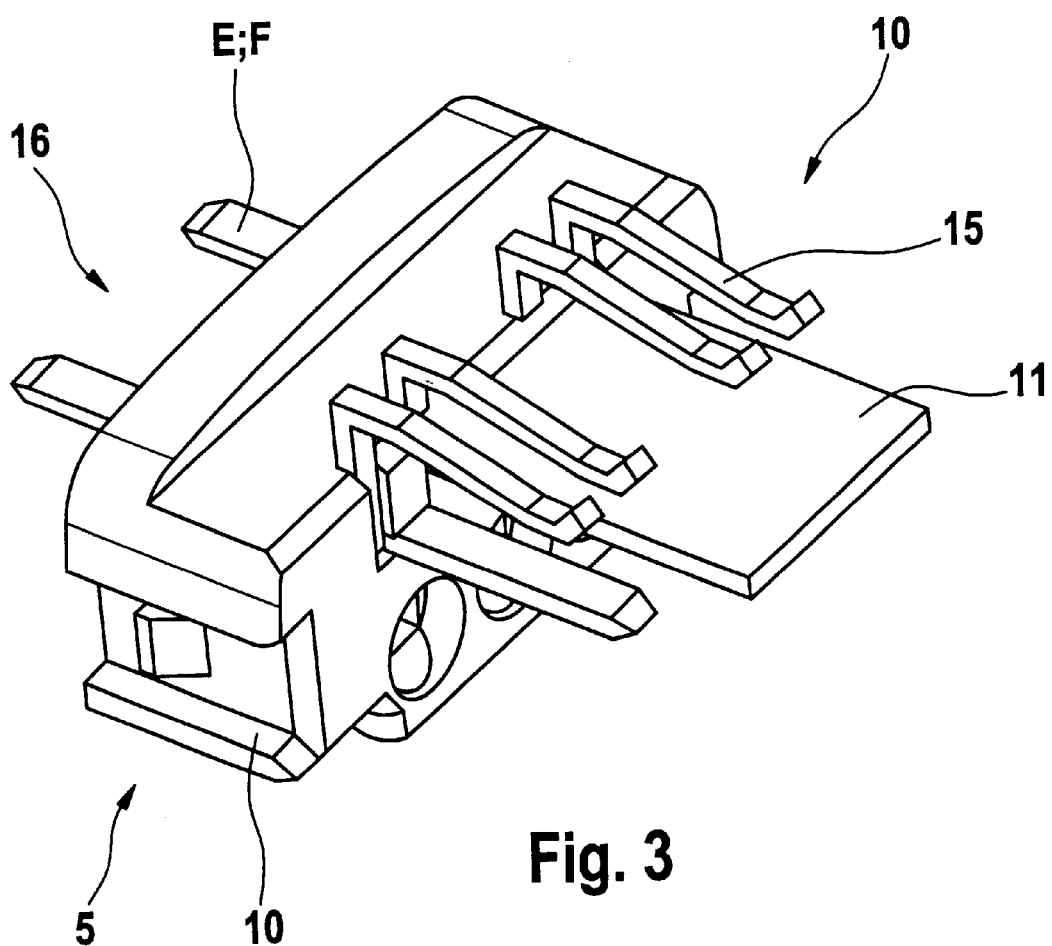
FIG. 3 shows a perspective view of the contact carrier of the coupler plug shown in FIG. 1, in pre-assembled state.

Coupler plug 1 shown in FIGS. 1 to 3 includes a housing 2, which includes a basic carrier 3 and a cover element 4, and a contact carrier 5.

Basic carrier 3 may include a single injection-molded component in which recesses, holes and openings in which electrical components can be placed, are provided. In particular, these components may include, for example, flat plug F, electrical contacts E, pressure compensation elements D, etc.

Cover element 4 can be placed on basic carrier 3. A seal 6 may be arranged between basic carrier 3 and cover element 4. Alternatively, seal 6 may also be injection molded directly onto cover element 4, thus ensuring it cannot be lost. To ensure that a seal is created between basic carrier 3 and the inside of cover element 4, a locking arrangement 7 is also provided. Locking arrangement 7 includes, for example, a preliminary locking arrangement 8, which includes an element that protrudes from basic (body) carrier 3 and engages with a recess 9 on the side of cover element 4.

Contact carrier 5, as is shown in particular in FIGS. 1 and 3, is a single plastic injection-molded component. It also has recesses, holes and openings in which electrical components can be placed.

In accordance with the present invention, contact carrier 5 is pre-mounted in the rest of coupler plug 1 before assembly. In one exemplary embodiment, which is shown by way of example in FIG. 1, electrical contacts E and flat plugs F have already been introduced, for example, having been welded or pressed in.

Contact carrier 5 also has guide elements 10, which ensure that contact carrier 5 can only be joined to the rest of coupler plug 1 in one specific single position. In addition, a stop-lock arrangement is provided on contact carrier 5, so that coupler plug 1 can be assembled without tools.

In the case of a further exemplary embodiment, as is shown by way of example in FIG. 3, in addition to electrical contacts E and flat plugs F, an adjustment element 11 for the Lambda sensor, which can be attached to coupler plug 1, is provided and may be soldered to electrical contacts E and flat plugs F.

Adjustment element 11, which in the case of the exemplary embodiment shown in FIG. 1 is arranged in basic (body) carrier 3 of coupler plug 1, includes a resistor layer arranged on a ceramic substrate. Alternatively, an electronic component specifically for adjustment may be provided. Adjustment element 11 is in electrical contact with contact elements 15, which simultaneously press adjustment element 11 against basic (body) carrier 3. To accomplish this, they are designed as spring-like clips.

Electrical contact elements 15 are shaped metal strips similar to printed conductors, and one side of them ends at coupling area 16 (shown in particular in FIG. 1) of coupler plug 1.

In addition, a secondary interlock element 12 is provided for assembly of coupler plug 1, and constitutes a connecting element between contact carrier 5 and basic carrier 3. Secondary interlock element 12 also has a guide arrangement, due thanks to which secondary interlock element 12 can only be joined to the rest of coupler plug 1 and contact carrier 5 if it is in one specific single position.

Secondary interlock element 12 also fixes in position the electrical components, e.g., electrical contacts and flat plugs, that are arranged in housing 2 of coupling plug 1. It is also used as a way of checking that coupler plug 1 is covered by cover element 4 in the functionally correct manner, in that cover element 4 can only be closed completely if the electrical components inside coupler plug 1 are fixed in position in their functionally correct manner.

To accomplish this, in its mounted state secondary interlock element 12 has at least one support element 13 that extends in the direction of cover element 4. This support element 13 is positioned so that if the electrical components are not fixed in position in the functionally correct manner by secondary interlock element 12, cover element 4 cannot be closed due to the length of support element 13, which protrudes beyond housing 2 of coupler plug 1.

Securing devices 18 (not shown in detail in the drawings) are provided on the outer periphery 14 of coupler plug 1, and are designed so that the entire coupler plug 1 can be attached via a groove-tongue connection or some other type of connection to a suitable component or to another object, e.g., a tube or an electrical line.

In addition, securing devices 18 may be used to attach appropriate electrical lines to coupler plug 1.

Due to the embodiment of coupler plug 1, it can be very compact and can have small dimensions, so that if necessary it can be used in applications involving very restricted space. In addition, coupler plug 1 according to the present invention has a small number of components, so that it can be manufactured inexpensively.

What is claimed is:

1. A coupler plug for a planar Lambda sensor, comprising:
   a housing including a basic element, a cover element, and a contact carrier, the contact carrier having electrical contacts pre-mounted thereon;
   electrical components inserted into the housing and fixed in position; and
   an adjustment element for the planar broadband Lambda sensor, the adjustment element being arranged one of: i) in the coupler plug, and ii) outside the coupler plug via a further contact element, the adjustment element being pre-mounted on the contact carrier, the contact carrier, electrical contacts and adjustment element being configured to separate from remaining portions of the coupler plug.

2. The coupler plug according to claim 1, wherein the cover element is configured to be slipped on the adjustment element.

3. A coupler plug for a planar Lambda sensor, comprising:
   a housing including a basic element, a cover element, and a contact carrier, the contact carrier having electrical contacts pre-mounted thereon;
   electrical components inserted into the housing and fixed in position;
   an adjustment element for the planar broadband Lambda sensor, the adjustment element being arranged one of in the coupler plug and outside the coupler plug via a further contact element, wherein the adjustment element is pre-mounted on the contact carrier, and the contact carrier, electrical contacts and adjustment element are separable from remaining portions of the coupler plug; and
   a primary interlock element and a secondary interlock element that works in conjunction with the cover element, the secondary interlock element including at least one support element that extends towards the cover element so that the cover element only closes completely if the secondary interlock element is in its final position.

4. The coupler plug according to claim 1, wherein the cover element is transparent.

5. The coupler plug according to claim 3, wherein the cover element has a low coefficient of absorption for monochromatic light.

6. The coupler plug according to claim 3, wherein the cover element has a low coefficient of absorption for laser light.

7. The coupler plug according to claim 1, further comprising:
   spring-like holding clips configured to hold the adjustment element against the housing.

8. The coupler plug according to claim 7, wherein the spring-like holding clips are electrical contact elements.

9. The coupler plug according to claim 1, wherein the electrical components are plug contacts.

10. The coupler plug according to claim 7, wherein the electrical components are plug contacts and wherein the spring-like holding clips and the plug contacts are electrically connected to one another.

11. The coupler plug according to claim 7, wherein the electrical components are plug contacts and wherein the spring-like holding clips and the plug contacts constitute a one-piece component.

12. The coupler plug according to claim 8, wherein the electrical contact elements and the adjustment element are coupled together via soldered joints.

13. The coupler plug according to claim 1, further comprising:
   a locking arrangement provided between the basic element and the cover element.

14. The coupler plug according to claim 1, further comprising:
   a mechanism for initial locking and final locking.

15. The coupler plug according to claim 1, further comprising:
   a securing device provided at a periphery of the cover element.

16. The coupler plug according to claim 15, wherein the securing device is designed as a groove, with which a tongue engages.

17. The coupler plug according to claim 15, wherein the securing device constitutes a holder for electrical lines.

18. The coupler plug according to claim 1, further comprising:
   an arrangement configured to attach a spray protection grommet, the arrangement being provided on the cover element.

19. The coupler plug according to claim 1, wherein the contact carrier is configured to lock into a remaining portion of the coupler plug.

20. The coupler plug according to claim 1, wherein at least one of the electrical contacts and the adjustment element are pressed into the contact carrier.

21. The coupler plug according to claim 20, wherein the electrical contacts are flat plugs.

* * * * *